US008469888B2

United States Patent
Lee et al.

(10) Patent No.: US 8,469,888 B2
(45) Date of Patent: Jun. 25, 2013

(54) FORMATION OF AN ENHANCED ELASTIC IMAGE IN AN ULTRASOUND SYSTEM

(75) Inventors: Kwang Ju Lee, Seoul (KR); Jong Sik Kim, Seoul (KR); Ra Young Yoon, Seoul (KR); Mok Kun Jeong, Seoul (KR)

(73) Assignee: Medison Co., Ltd.

( * ) Notice: Subject to any disclaimer, the term of this patent is extended or adjusted under 35 U.S.C. 154(b) by 812 days.

(21) Appl. No.: 12/491,168

(22) Filed: Jun. 24, 2009

(65) Prior Publication Data

US 2009/0326378 A1 Dec. 31, 2009

(30) Foreign Application Priority Data

Jun. 26, 2008 (KR) ........................ 10-2008-0060540

(51) Int. Cl.
*A61B 8/00* (2006.01)

(52) U.S. Cl.
USPC .......................................................... 600/437

(58) Field of Classification Search
None
See application file for complete search history.

(56) References Cited

U.S. PATENT DOCUMENTS

| | | | | |
|---|---|---|---|---|
| 5,669,387 | A * | 9/1997 | Mine ............................ | 600/455 |
| 6,514,204 | B2 * | 2/2003 | Alam et al. .................... | 600/442 |
| 2004/0215075 | A1 | 10/2004 | Zagzebski et al. | |
| 2006/0052696 | A1 * | 3/2006 | Shiina et al. .................. | 600/437 |
| 2006/0084870 | A1 | 4/2006 | Kim et al. | |
| 2006/0170714 | A1 * | 8/2006 | Kanda ............................. | 346/2 |
| 2007/0038090 | A1 | 2/2007 | Moon et al. | |
| 2007/0197915 | A1 * | 8/2007 | Jeong et al. .................... | 600/459 |
| 2008/0064956 | A1 | 3/2008 | Jeong et al. | |
| 2008/0087089 | A1 | 4/2008 | Nam | |
| 2008/0188743 | A1 * | 8/2008 | Waki et al. .................... | 600/438 |

FOREIGN PATENT DOCUMENTS

| | | |
|---|---|---|
| EP | 1079240 A2 | 2/2001 |
| JP | 2005-334196 A | 12/2005 |
| JP | 2006-110360 | 4/2006 |
| JP | 2006-174902 A | 7/2006 |
| JP | 2006-524115 | 10/2006 |

(Continued)

OTHER PUBLICATIONS

Extended European Search Report for Patent Application No. 09163584.7-2319, mailed Oct. 16, 2009, 5 pages.

(Continued)

*Primary Examiner* — Long V. Le
*Assistant Examiner* — Lawrence Laryea
(74) *Attorney, Agent, or Firm* — McDermott Will & Emery LLP

(57) ABSTRACT

There are disclosed embodiments for forming an enhanced elastic image in an ultrasound system. An elastic image of a target object may be formed by scanning N scan lines. A control unit divides the N scan lines into M scan lines groups by using an acquisition period necessary for transmitting and receiving ultrasound signals to acquire ultrasound data. An ultrasound data acquiring unit transmits ultrasound signals to a target object and receives the ultrasound signals reflected from the target object at a predetermined transmission/reception sequence for each of the M scan line groups. This forms ultrasound data corresponding to each of the M scan line groups while a pressure is applied to the target object. An elastic image forming unit forms at least one sub elastic image corresponding to each of the M scan line groups based on the ultrasound data. The elastic forming unit sums M sub elastic images corresponding to the respective M scan line groups to thereby form an elastic image of the target object.

14 Claims, 2 Drawing Sheets

FOREIGN PATENT DOCUMENTS

| | | |
|---|---|---|
| JP | 2007-029737 | 2/2007 |
| JP | 2008-100068 A | 5/2008 |
| KR | 10-2008-0024327 | 3/2008 |
| KR | 10-2008-0028658 | 4/2008 |
| WO | WO 2004/093671 A2 | 11/2004 |
| WO | WO 2007/049228 A1 | 5/2007 |
| WO | WO2006022238 * | 5/2007 |
| WO | WO 2008/027520 A2 | 3/2008 |

OTHER PUBLICATIONS

Korean Office Action issued in Korean Patent Application No. 10-2008-0060540, mailed Jan. 12, 2011.

Japanese Office Action issued in Japanese Patent Application No. JP 2009-152580 dated Jul. 19, 2011.

* cited by examiner

FORMATION OF AN ENHANCED ELASTIC IMAGE IN AN ULTRASOUND SYSTEM

The present application claims priority from Korean Patent Application No. 10-2008-0060540 filed on Jun. 26, 2008, the entire subject matter of which is incorporated herein by reference.

TECHNICAL FIELD

The present disclosure generally relates to ultrasound systems, and more particularly to an ultrasound system for forming an enhanced elastic image.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

Generally, the ultrasound image is displayed in a Brightness-mode (B-mode) by using reflectivity caused by an acoustic impedance difference between the tissues of the target object. However, if the reflectivity of the target object is hardly different from those of the neighboring tissues such as tumor, cancer or the like, then it is not easy to recognize the target object in the B-mode image. Further, an ultrasound elastic imaging technology has been developed to display an image of the target object by using mechanical characteristics of the target object such as the elasticity of the target object. Such technology is very helpful for diagnosing lesions such as tumor and cancer. The tumor or cancer is relatively stiffer than the neighboring tissues. Thus, when stress is uniformly applied, a displacement of the tumor or cancer is typically smaller than those of the neighboring tissues.

The elasticity of a tissue is measured by using ultrasound data obtained before and after compressing the tissue. A pressure plate mounted on a front side of an ultrasound probe is used to compress the tissue. A user may press the pressure plate on the target object, for example, by using an ultrasound probe to thereby compress the tissues of the target object. In such a case, since strain in the tissues depends on the pressure applied by the user, the quality of an elastic image may be changed according to the pressure applied to the tissue. For example, if the pressure is relatively weak, then a difference in strain between the tumor or cancer tissue and the neighboring tissues thereof tends to be very small, while the tumor or cancer is hardly distinguishable from the neighboring tissues in the elastic image.

Further, if the pressure is relatively hard, then a correlation between the tumor or cancer tissue and the neighboring tissues is lowered, which results in deterioration of the quality of the elastic. Thus, an appropriate pressure is required to obtain an enhanced elastic image. Experimentally, when the strain of the tissues falls within a range of 1-3%, an optimal elastic image can be obtained.

Since the ultrasound elastic image is formed by obtaining ultrasound data in a frame unit, a pressing speed and a frame rate may be important factors in determining the quality of the elastic image. Assuming that the target object is a breast whose elastic image is commonly used, a thickness of the target object may be about 30 mm. When the target object is compressed by applying a pressure, a moving speed of a user's hand may be about 10 mm/s. Under the above conditions, an appropriate frame rate to obtain an average strain of 1% may be determined by the following equation (1).

$$\text{Frame rate} > (10 \text{ mm/sec})/(0.3 \text{ mm/frame}) = 33 \text{ frames/sec} \quad (1)$$

That is, when the frame rate becomes greater than 33 frames/sec, the average strain may be less than 1%. Otherwise, if the frame rate is lower than 33 frames/sec, then the strain may be increased over 1%, which may cause an error for determining a correlation between the lesion and neighboring tissues.

However, in case of obtaining ultrasound image data at a rate of at least 33 frames/sec, the number of scan lines for obtaining the ultrasound image data should be reduced. This may cause a problem since the quality of 2-dimensional black and white (BW) ultrasound image is lowered. Also, as the depth of the lesion becomes deeper, the frame rate may be lowered due to the physical characteristic of the ultrasound signals propagated into the target object. This also makes the quality of the ultrasound elastic image degraded. Further, to achieve the above frame rate, the user has to press the target object at the corresponding pressing speed.

SUMMARY

Embodiments for forming an enhanced elastic image in an ultrasound system by using ultrasound data obtained in an acquisition period while applying a pressure to a target object are disclosed herein. In one embodiment, by way of non-limiting example, an ultrasound system for forming an elastic image of a target object, comprises: an input unit operable to allow a user to input an acquisition period; a control unit operable to divide N scan lines into M scan line groups by using the acquisition period, wherein N and M are a positive integer and N is greater than M; an ultrasound data acquisition unit operable to perform plural transmissions/receptions of ultrasound signals to/from a target object with a pressure applied thereto for the M scan line groups in an ordered sequence thereof to thereby form a plurality of ultrasound data corresponding to each of the M scan line groups, wherein each of the plural transmissions/receptions is performed within the acquisition period; and an elastic image forming unit operable to form at least one sub-elastic image corresponding to each of the M scan line groups based on the ultrasound data, the elastic forming unit being further operable to sum the M sub-elastic images corresponding to the respective M scan line groups to thereby form an elastic image of the target object.

In one embodiment, a method of forming an elastic image of a target object, comprises: a) receiving an acquisition period representing time duration necessary for transmitting and receiving ultrasound signals to acquire ultrasound data; b) dividing N scan lines into M scan lines groups by using the acquisition period, wherein N and M are a positive integer and N is greater than M; c) performing plural transmissions/receptions of ultrasound signals to/from a target object with a pressure applied thereto for the M scan line groups in an ordered sequence thereof to thereby form a plurality of ultrasound data corresponding to each of the M scan line groups, wherein each of the plural transmissions/receptions is performed within the acquisition period; and d) forming at least one sub-elastic image corresponding to each of the M scan line groups based on the ultrasound data, and summing the M sub-elastic images corresponding to the respective M scan line groups to thereby form an elastic image of the target object.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
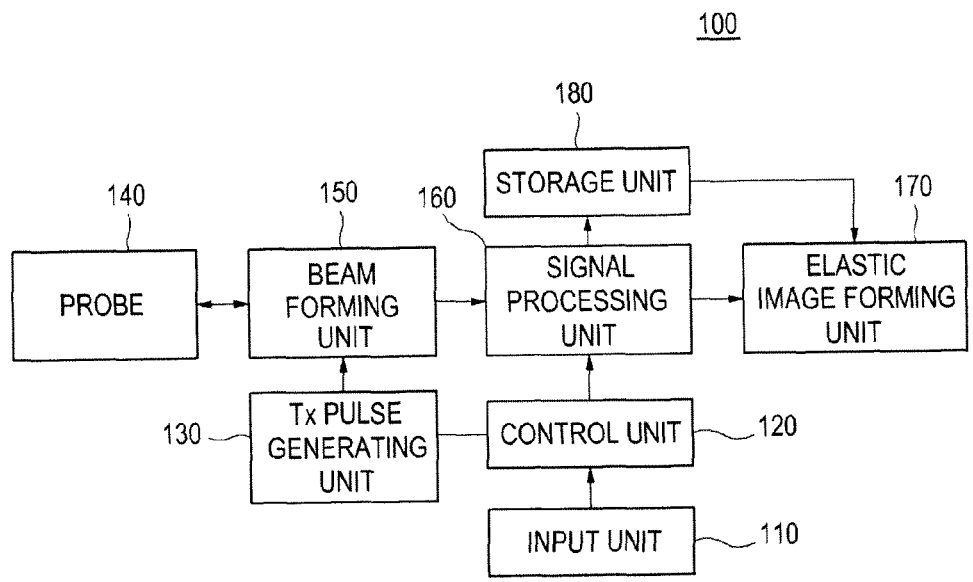
FIG. 1 is a block diagram showing an illustrative embodiment of an ultrasound system.

FIG. 1 is a block diagram showing an illustrative embodiment of an ultrasound system. The ultrasound system 100 may include an input unit 110 operable to allow a user to input an acquisition period. The acquisition period may be a time duration for acquiring ultrasound data by transmitting and receiving ultrasound signals to/from a target object at one time. In one embodiment, the acquisition period may be set by the user. Alternatively, the acquisition period may be selected among candidate acquisition periods provided by the ultrasound system. The input unit 110 may be further operable to allow the user to select a desired image mode.

The ultrasound system 100 may further include a control unit 120 that may be operable to control an operation of the ultrasound system 100 based on the acquisition period and the selection of the image mode. A detailed description for an operation of the control unit 120 will be described later.

The ultrasound system 100 may further include a transmit (Tx) pulse generating unit 130 and a probe 140 including an array transducer consisting of a plurality of elements. The Tx pulse generating unit 130 may be operable to generate Tx pulse signals for application to the elements of the probe 140. The elements may be operable to reciprocally convert electrical pulse signals and ultrasound signals. The probe 140 may include a transmission/reception (Tx/Rx) plane (not shown), which may be in contact with the surface of the target object. Ultrasound signals may be transmitted through the Tx/Rx plane of the probe 140 in response to the Tx pulse signals. The probe 140 may further include a pressure plate (not shown). The pressure plate may be configured to encompass and extend the Tx/Rx plane. However, its shape is not limited thereto.

The ultrasound system 100 may further include a beam forming unit 150. The beam forming unit 150 may apply delays to the Tx pulse signals to form a transmit pattern such that the ultrasound signals transmitted from the probe 140 focus on scan lines.

The probe 140 may be further operable to receive ultrasound echo signals reflected from the target object and convert them into electrical receive signals. The beam forming unit 150 may be further operable to apply delays to the receive signals outputted from the probe 140 in consideration of distances between the elements and the focal points. It may then sum the delayed receive signals to thereby form a receive-focused beam.

The ultrasound system 100 may further include a signal processing unit 160. The signal processing unit 160 may be operable to perform signal processing upon the receive-focused beam to thereby form ultrasound data. The signal processing unit 160 may be operable to form the ultrasound data in the acquisition period. The formed ultrasound data may be stored in a storage unit 180. The storage unit 180 may include a buffer for temporarily storing the ultrasound data.

The ultrasound system 100 may further include an elastic image forming unit 170. The elastic image forming unit 170 may be operable to search the storage unit 180 to check whether the ultrasound data are stored for all of the scan lines. If the acquisition of the ultrasound data is completed for all of the scan lines, then the elastic image forming unit 170 may be operable to analyze the ultrasound data to form an elastic image. In one embodiment, the analysis of the ultrasound data may be carried out by auto-correlation.

Figure 2:
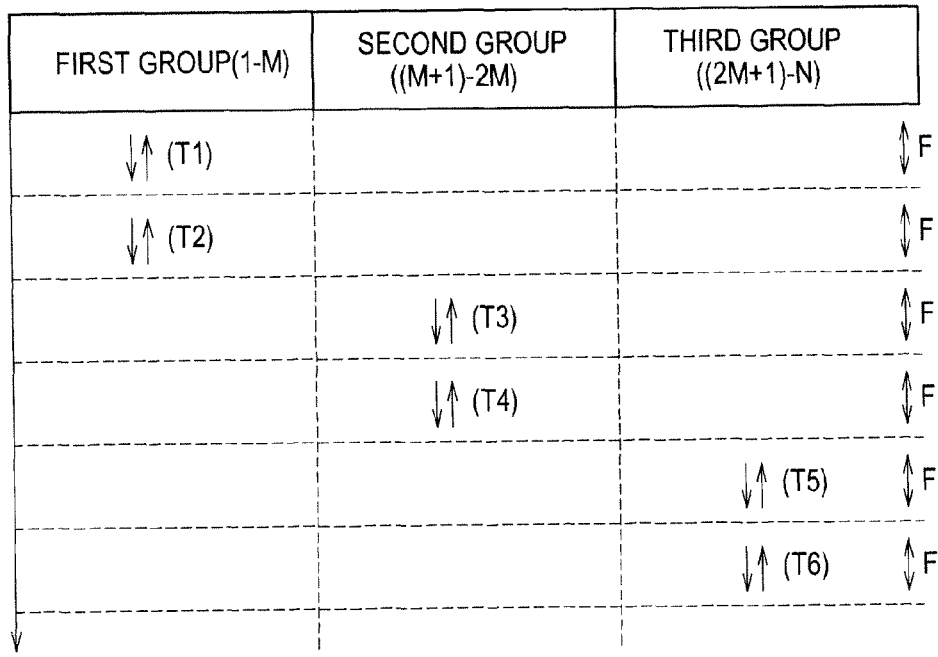
FIG. 2 shows an example of a transmission/reception ordered sequence of ultrasound signals.

Hereinafter, a method of forming the elastic image will be described in detail with reference to FIGS. 1 and 2. FIG. 2 is a schematic diagram showing an example of a transmission/reception ordered sequence of ultrasound signals in one embodiment. For the sake of convenience, an example of setting N scan lines necessary for acquiring one frame of the elastic image will be described, wherein N is a positive integer.

If the acquisition period F is determined according to the user's input through the input unit 110, then the control unit 120 may be operable to calculate the maximum number of scan lines, Smax, for which the ultrasound data can be obtained during the acquisition period. The maximum number of the scan lines, Smax, may be calculated according to the following equation (2).

$$Smax = (1/F)/Tos \qquad (2)$$

wherein Tos represents time duration necessary for acquiring ultrasound data corresponding to one scan line. The Tos may be obtained as the following equation (3).

$$Tos = Dv/C + Tsd \qquad (3)$$

wherein Dv represents a view depth of an elastic image to be formed and C represents a sound speed in the target object (e.g., about 1540 mm/s in a human body). Also, Tsd represents a time duration, within which ultrasound signals are transmitted and received at one time, in the ultrasound system.

The control unit 120 may be further operable to divide the entire N scan lines into a plurality of scan line groups by using the maximum number of the scan lines, Smax, which is calculated according to equations (2) and (3). For example, assuming that the number of the scan lines, Smax, is M, the N scan lines may be divided into a first scan line group including (1–M) scan lines, a second scan line group including ((M+1)–2M) scan lines and a third scan line group including ((2M+1)–N), as illustrated in FIG. 2. After determining the scan line groups, the control unit 120 may be operable to determine a transmission/reception ordered sequence of the respective scan line groups. The control unit 120 may be operable to control transmission/reception of the ultrasound signals based on the transmission/reception ordered sequence.

In one embodiment, while a pressure is applied to the target object, the control unit 120 may be operable to control operations of the Tx pulse generating unit 130, probe 140 and beam forming unit 150 such that the ultrasound signals are transmitted twice, T1 and T2 to be focused along the first scan line group in the acquisition period so that first and second ultrasound data corresponding to the first scan line group may be acquired. The first and second ultrasound data may be stored in the storage unit 180.

Subsequently, under the control of the control unit 120, the ultrasound signals may be transmitted twice, T3-T4 and T5-T6 to the second and third scan line groups, respectively, in the same manner of the transmission/reception to the first scan line group while the pressure is applied to the target object. This is so that the first and second ultrasound data corresponding to the respective scan line groups may be obtained. In one embodiment, the first ultrasound data acquired for the respective scan line groups may be considered as the ultrasound data acquired before applying the pressure. Further, the second ultrasound data acquired for the respective scan line groups may be considered as the ultrasound data acquired after applying the pressure.

If the acquisition of the first and second ultrasound data for all of the scan line groups is completed, then the elastic image forming unit 170 may be operable to compare the first and second ultrasound data for the respective scan line groups. In one embodiment, a comparison of the first and second ultrasound data may be carried out by using the auto-correlation. The elastic image forming unit 170 may be operable to form sub-elastic images for the respective scan line groups based on the comparison results and then sum the sub-elastic images to thereby form a final elastic image of the target object. In one embodiment, the comparison of the first and second ultrasound data may be carried out by using the auto-correlation, although it is not limited thereto. Since the auto-correlation is a well-known method of comparing the data, detailed descriptions thereof will be omitted.

Figure 3:
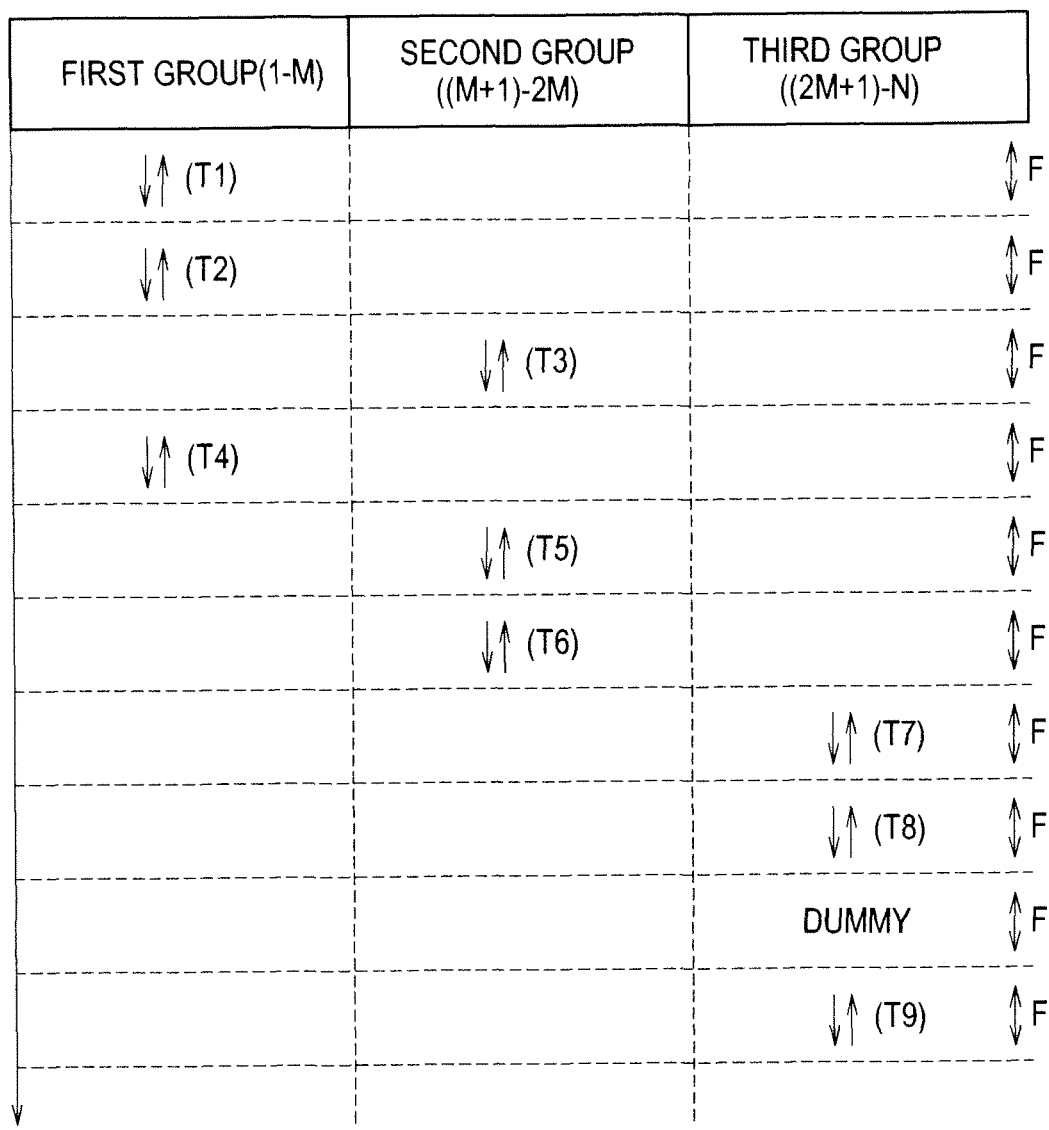
FIG. 3 shows an example of a transmission/reception ordered sequence of ultrasound signals according to another embodiment.

In one embodiment, a plurality of sub-elastic images may be formed by using different strains of the target object for each of the scan line groups. In such a case, the sub-elastic images corresponding to the same strain may be summed so that a plurality of final elastic images of the target object may be formed. This elastic image forming method will be described in detail with reference to the FIGS. 1 and 3. FIG. 3 is a schematic diagram showing an example of a transmission/reception ordered sequence of the scan line groups in one embodiment. For the sake of convenience, an example of setting N scan lines necessary for acquiring one frame of the elastic image will be described, wherein N is a positive integer.

If the acquisition period F is determined according to the user's input through the input unit 110, then the control unit 120 may be operable to calculate the maximum number of scan lines, Smax, for acquiring the ultrasound data during the acquisition period among the N scan lines, as mentioned above.

The control unit 120 may be further operable to divide the entire N scan lines into a plurality of scan line groups by using the maximum number of the scan lines, Smax, which is calculated through equations (2) and (3). For example, assuming that the number of the scan lines, Smax, is M, the N scan lines may be divided into a first scan line group including (1−M) scan lines, a second scan line group including ((M+1)−2M) scan lines and a third scan line group including ((2M+1)−N) scan lines, as illustrated in FIG. 3. After determining the scan line groups, the control unit 120 may be operable to determine a transmission/reception ordered sequence of the ultrasound signals for the respective scan line groups. The control unit 120 may be operable to control transmission/reception of the ultrasound signals based on the transmission/reception ordered sequence. That is, the transmission/reception of the ultrasound signals may be carried out for the respective scan line groups according to the transmission/reception ordered sequence.

In one embodiment, while a pressure is applied to the target object by using the probe, the ultrasound signals may be transmitted twice, T1 and T2, in the acquisition period to be focused along the first scan line group. This is so that first and second ultrasound data corresponding to the first scan line group may be acquired by using reflected ultrasound signals. The transmission/reception of the ultrasound signals may be carried out according to the transmission/reception ordered sequence under the control of the control unit 120. The first and second ultrasound data may be stored in the storage unit 180.

Subsequently, ultrasound signals may be transmitted once T3 to be focused along the second scan line group. This is so that first ultrasound data corresponding to the second scan line group may be acquired by using reflected ultrasound signals. Thereafter, ultrasound signals may be transmitted once, T4, to be focused along the first scan line group in the acquisition period so that third ultrasound data corresponding to the first scan line group may be acquired. The third ultrasound data may be also stored in the storage unit 180.

Successively, ultrasound signals are transmitted twice, T5 and T6. to be focused along the second scan line group in the acquisition period so that second and third ultrasound data corresponding to the second scan line group may be acquired. The second and third ultrasound data corresponding to the second scan line group may be also stored in the storage unit 180. Thereafter, ultrasound signals are transmitted twice, T7 and T8, to be focused along the third scan line group in the acquisition period so that first and second ultrasound data corresponding to the third scan line group may be acquired. In one embodiment, the control unit 120 may be operable to control the transmission of the ultrasound signals to have a dummy time identical to one acquisition period. Then, the ultrasound signals are transmitted once, T9, to be focused along the third scan line group so that third ultrasound data corresponding to the third scan line group may be acquired. The first to third ultrasound data corresponding to the third scan line group may be also stored in the storage unit 180.

In one embodiment, the elastic image forming unit 170 may be operable to compare the first, second and third ultrasound data for each of the scan line groups to thereby form sub-elastic images. Assuming that the strain of 1% may occur during one acquisition period while the pressure is applied to the target object, a first sub-elastic image formed based on the strain of 1%, a second sub-elastic image formed based on the strain of 2% and a third sub-elastic image formed based on the strain of 3% may be obtained for each of the scan line groups. For example, the strain between the first ultrasound data and the second ultrasound data corresponding to the first scan line group may be 1%, while the strain between the second ultrasound data and the third ultrasound data corresponding to the first scan line group may be 2%. Also, the strain between the first ultrasound data and the third ultrasound data corresponding to the first scan line group may be 3%. Thus, the ultrasound data having a predetermined range of strain 1%-3% may be acquired.

The elastic image forming unit 170 may be further operable to sum the sub-elastic images formed based on the same strain for the respective scan line groups to thereby form elastic images of the target object corresponding to strains of 1%, 2% and 3%. Further, the elastic image forming unit 170 may be operable to average the elastic images of the target object to thereby form a final elastic image of the target object. In one embodiment, as mentioned above, the elastic images are formed at various strains and the elastic images are compounded. Thus, although the pressure may not be uniformly applied to the target object, an error of data necessary for forming the elastic image may be reduced.

In one embodiment, when the number of the scan line groups is an even number, the control unit 120 may be operable to pair the M scan line groups. In such a case, the dummy time may not be needed.

Although the strains for forming the elastic images are described for 1%, 2% and 3% in one embodiment, the strains are not limited thereto. Various strains may be adopted according to types of target object by adjusting the transmission/reception ordered sequence of the ultrasound signals. For example, the strains of 1%-5%, 2%-3% or 1.5%-3.5% may be adopted to form the sub-elastic images and then the sub-elastic images summed and averaged to form a final elastic image of the target object. A method of forming the elastic image by using the strain of the target object is well known to a person skilled in the art. Thus, detailed description thereof is omitted. In one embodiment, the formation of the elastic image may be carried out by referring to the methods disclosed in Korean Patent Nos. 10-686288 and 10-782045 owned by Medison Co. LTD.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system for forming an elastic image of a target object, comprising:
    an input unit operable to allow a user to input an acquisition period representing time duration necessary for transmitting and receiving ultrasound signals to acquire ultrasound data;
    a control unit operable to divide N scan lines into M scan line groups by using the acquisition period and to determine a transmission/reception ordered sequence of the respective M scan line groups, wherein N and M are a positive integer and N is greater than M;
    an ultrasound data acquisition unit operable to perform plural transmissions/receptions of ultrasound signals to/from a target object with a pressure applied thereto for the M scan line groups in the transmission/reception ordered sequence thereof to thereby form a plurality of ultrasound data corresponding to each of the M scan line groups, wherein each of the plural transmissions/receptions is performed within the acquisition period; and
    an elastic image forming unit operable to form at least one sub-elastic image corresponding to each of the M scan line groups based on the ultrasound data, the elastic forming unit being further operable to sum the M sub-elastic images corresponding to respective M scan line groups to thereby form an elastic image of the target object.

2. The ultrasound system of claim 1, wherein the ultrasound data acquisition unit is operable to sequentially transmit the ultrasound signals twice in the acquisition period to thereby acquire first ultrasound data and second ultrasound data for each of the M scan line groups, and
    wherein elastic image forming unit is operable to compare the first ultrasound data and the second data, and form the M sub-elastic images corresponding to the M scan line groups based on a comparison result.

3. The ultrasound system of claim 2, wherein the control unit is operable to calculate a maximum number of scan lines within which the ultrasound data are obtained during the acquisition period and divide the N scan lines into the M scan line groups based on the maximum number of the scan lines.

4. The ultrasound system of claim 3, wherein the control unit calculates a maximum number (Smax) of the scan lines according to a following equation, $$Smax=(1/F)/Tos$$

where F represents the acquisition period and Tos represents a time duration necessary for acquiring ultrasound data for one scan line, and the Tos may be obtained according to the following equation, $$Tos=Dv/C+Tsd$$

where Dv represents a view depth of an elastic image to be formed, C represents a sound speed in the target object, Tsd represents a time duration necessary for transmitting and receiving ultrasound signals in the ultrasound system.

5. The ultrasound system of claim 2, wherein the ultrasound data acquisition unit is operable to further acquire third ultrasound data for each of the M scan line groups, and wherein the third ultrasound data are acquired at an interval of two acquisition periods from the acquisition of the first ultrasound data.

6. The ultrasound system of claim 1, wherein the ultrasound data acquisition unit is operable to multiply transmit/receive ultrasound signals multiple times to/from each of the M scan line groups in the acquisition period to form a plurality of ultrasound data corresponding to the respective M scan line group while the pressure is applied to the target object, and
    wherein the elastic image forming unit is operable to form a plurality of sub-elastic images corresponding to different strains for each of the M scan line groups, and sum the sub-elastic images corresponding to a same strain to thereby form elastic images of the target object for respective strains.

7. The ultrasound system of claim 6, wherein the elastic image forming unit is further operable to compound the elastic images of the target object for the respective strains.

8. A method of forming an elastic image of a target object, comprising:
    a) receiving an acquisition period representing time duration necessary for transmitting and receiving ultrasound signals to acquire ultrasound data;
    b) dividing N scan lines into M scan lines groups by using the acquisition period and determining a transmission/reception ordered sequence of the respective M scan line groups, wherein N and M are a positive integer and N is greater than M;
    c) performing plural transmissions/receptions of ultrasound signals to/from a target object with a pressure applied thereto for the M scan line groups in the transmission/reception ordered sequence to thereby form a plurality of ultrasound data corresponding to each of the M scan line groups, wherein each of the plural transmissions/receptions is performed within the acquisition period; and
    d) forming at least one sub-elastic image corresponding to each of the M scan line groups based on the ultrasound data, and summing the M sub-elastic images corresponding to respective M scan line groups to thereby form an elastic image of the target object.

9. The method of claim 8, wherein the c) includes transmitting the ultrasound signals twice in the acquisition period to thereby acquire first ultrasound data and second ultrasound data for each of the M scan line groups, and the d) includes comparing the first ultrasound data and the second data to form M sub-elastic images corresponding to the M scan line groups based on a comparison result.

10. The method of claim 8, wherein the c) includes:
   c1) pairing the M scan line groups to at least one pair of scan line groups;
   c2) transmitting the ultrasound signals twice in the acquisition period to be focused along a first scan line group in each pair of the scan line groups to form first and second ultrasound data corresponding to the first scan line group;
   c3) transmitting the ultrasound signals once to be focused along a second scan line group in each pair of the scan line groups to form first ultrasound data corresponding to the second scan line group;
   c4) transmitting the ultrasound signals once to be focused along the first scan line group in each pair of the scan line groups to form third ultrasound data corresponding to the first scan line group; and
   c5) transmitting the ultrasound signals twice in the acquisition period to be focused along the second scan line group in each pair of the scan line groups to form second and third ultrasound data corresponding to the second scan line group.

11. The method of claim 10, wherein the d) includes forming a first elastic image, a second elastic image and a third elastic image based on the first, second and third ultrasound data.

12. The method of claim 11, further comprising compounding the first, second and third elastic images.

13. The method of claim 8, wherein the N scan lines are divided into the M scan line groups by using a maximum number of scan lines for acquiring the ultrasound data during the acquisition period.

14. The method of claim 13, where the maximum number $S_{max}$ of the scan lines is calculated as a following equation, $$S_{max} = (1/F)/T_{os}$$

where F represents the acquisition period and $T_{os}$ represents time duration necessary for acquiring ultrasound data for one scan line, and the $T_{os}$ may be obtained as a following equation, $$T_{os} = D_v/C + T_{sd}$$

where $D_v$ represents a view depth of an elastic image to be formed, C represents a sound speed in the target object, $T_{sd}$ represents time duration for transmitting and receiving ultrasound signals in the ultrasound system.

\* \* \* \* \*